(12) United States Patent
Klemm

(10) Patent No.: US 6,435,186 B1
(45) Date of Patent: Aug. 20, 2002

(54) ANTERIOR SUPPORT DEVICE

(76) Inventor: Kurt Klemm, 4832 Ridge Rd., Rhinelander, WI (US) 54501

( * ) Notice: Subject to any disclaimer, the term of this patent is extended or adjusted under 35 U.S.C. 154(b) by 0 days.

(21) Appl. No.: 09/932,041

(22) Filed: Aug. 17, 2001

(51) Int. Cl.[7] .............................................. A61G 15/00
(52) U.S. Cl. ....................... 128/845; 248/161
(58) Field of Search ................... 128/845, 847; 482/148, 123, 129, 117, 114, 130, 142, 92, 101; 403/60, 90; 16/94 R, 96 R; 182/129; 601/27, 23, 34; 297/143; 606/240, 242; 5/630, 635; 248/161, 157, 407, 288.31, 288.51, 298.1

(56) References Cited

U.S. PATENT DOCUMENTS

| 135,435 A | * | 2/1873 | Lyon ............................ 248/161 |
| 2,038,806 A | * | 4/1936 | Sellar .......................... 248/161 |
| 2,519,771 A | * | 8/1950 | Lacore ....................... 248/298.1 |
| 4,397,374 A | * | 8/1983 | Rumage et al. .............. 182/129 |
| 5,118,062 A | * | 6/1992 | Archambault ............. 248/285.1 |
| 5,545,177 A | * | 8/1996 | Coseo .......................... 601/107 |
| 6,309,329 B2 | * | 10/2001 | Conner ........................ 482/122 |

* cited by examiner

Primary Examiner—Michael A. Brown
Assistant Examiner—Fenn Mathew
(74) Attorney, Agent, or Firm—McDonnell Boehnen Hulbert & Berghoff

(57) ABSTRACT

The present invention is directed to a device that supports an individual's spine while the individual is in a forward bent position. The device includes a padded rest on which an individual could lean while working in a forward bent position and brackets for adjusting the angle, height, and position of the device. Since the individual leans against the rest, the stresses experienced in the lower, middle and upper back are substantially decreased. Reducing such stress decreases the pain experienced by the individual as well as extends his or her productive life.

16 Claims, 5 Drawing Sheets

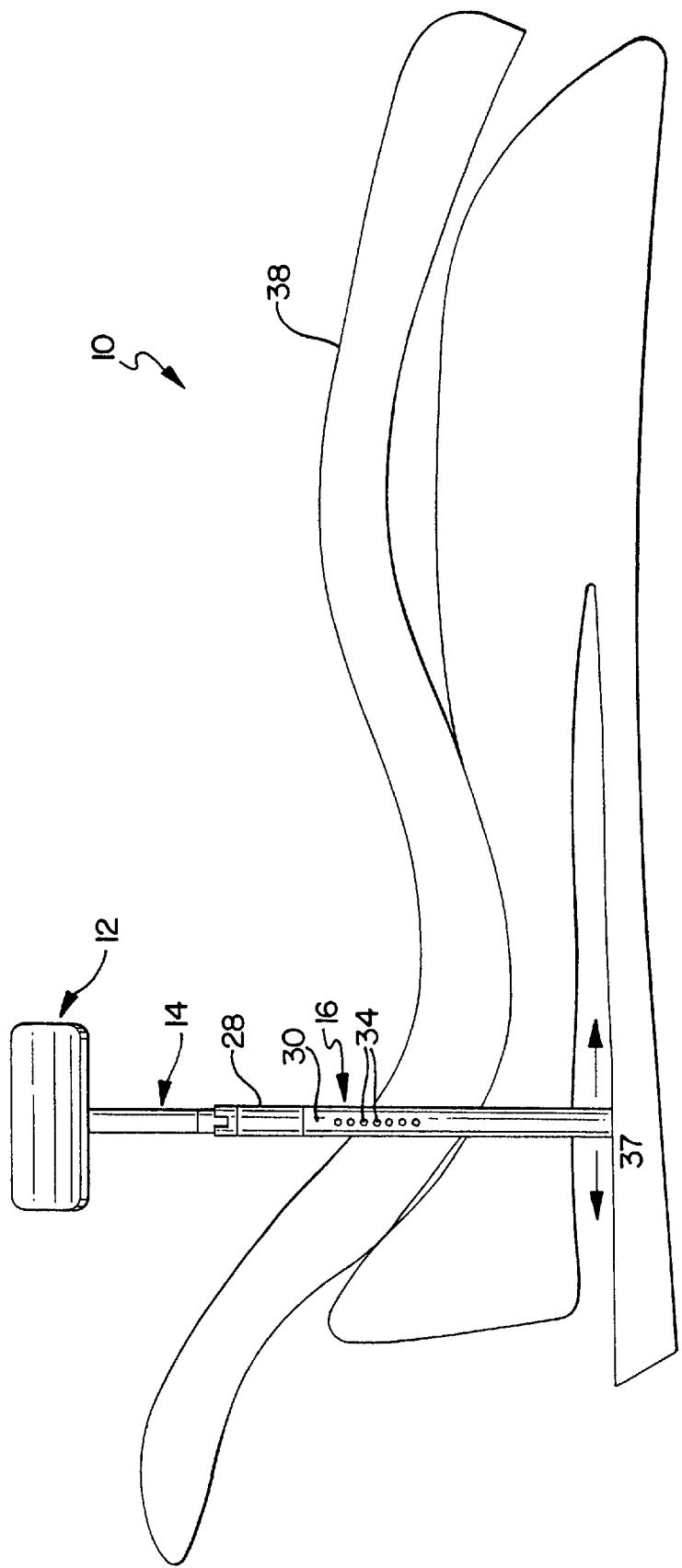

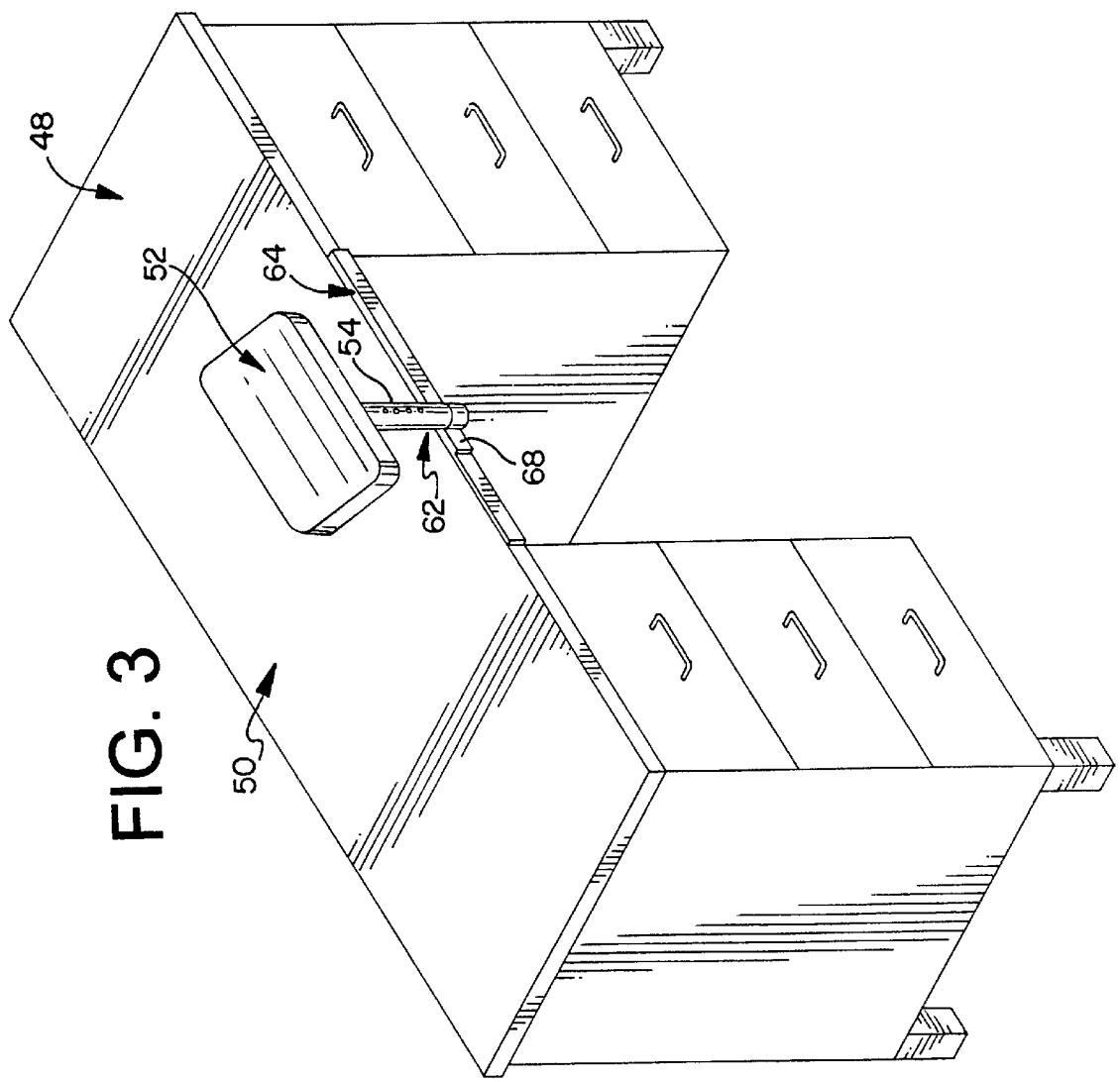
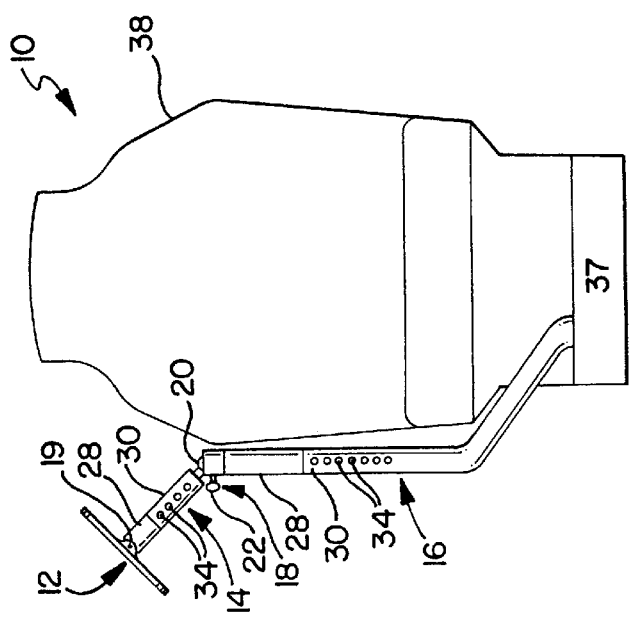

FIG. 5
FIG. 4
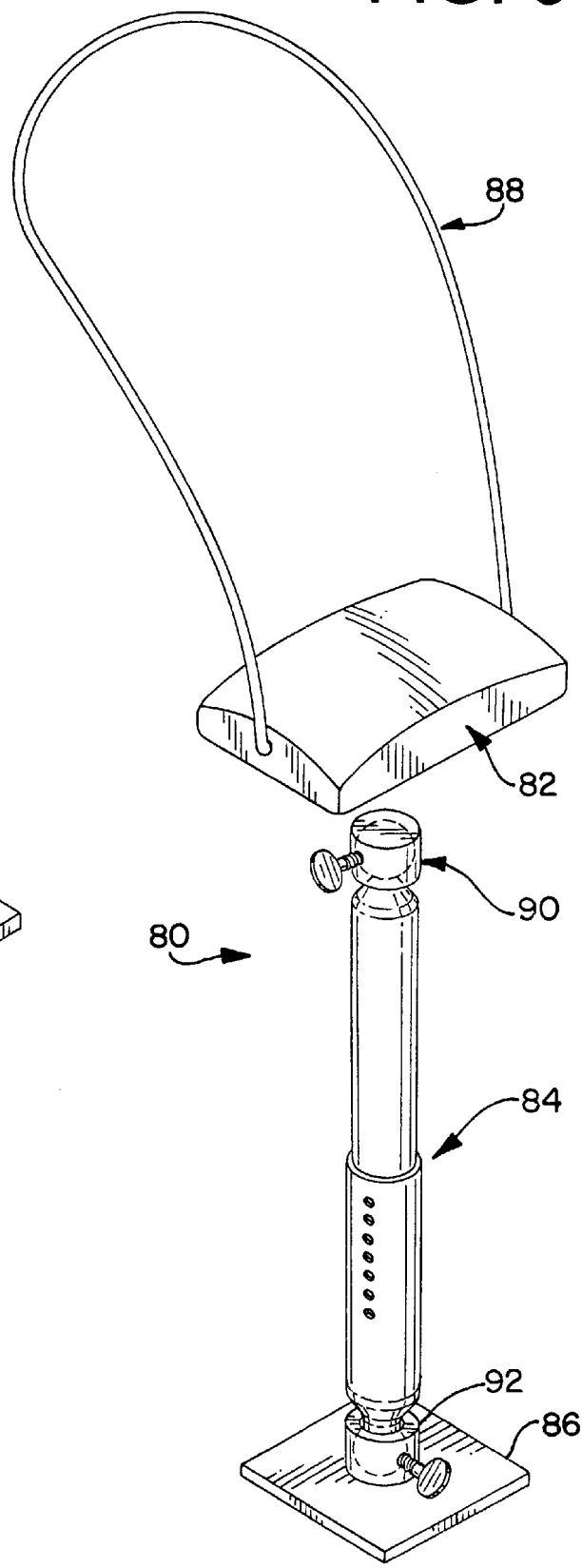
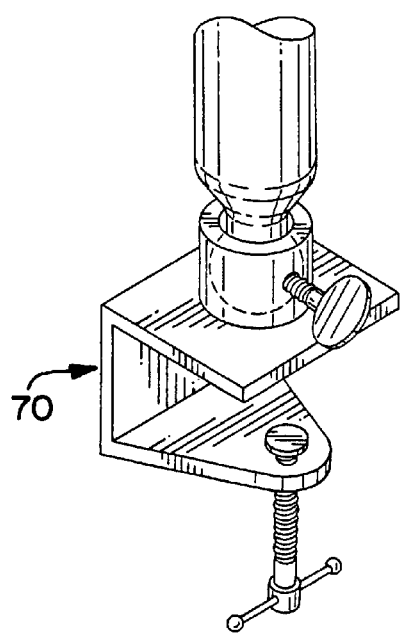

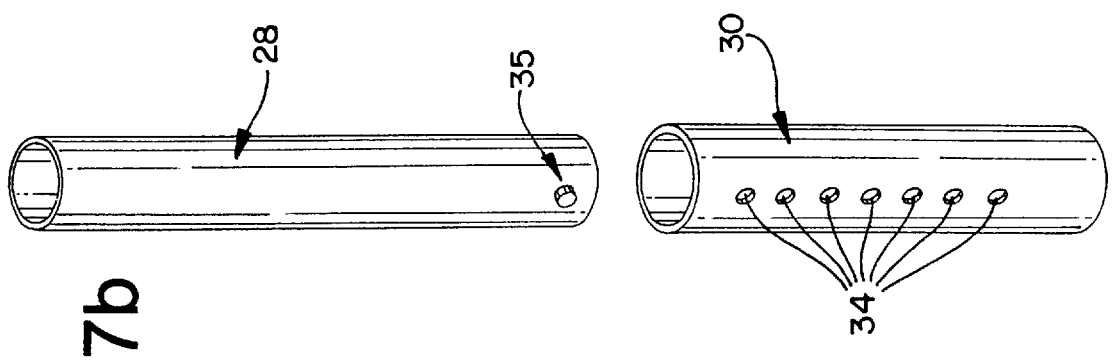
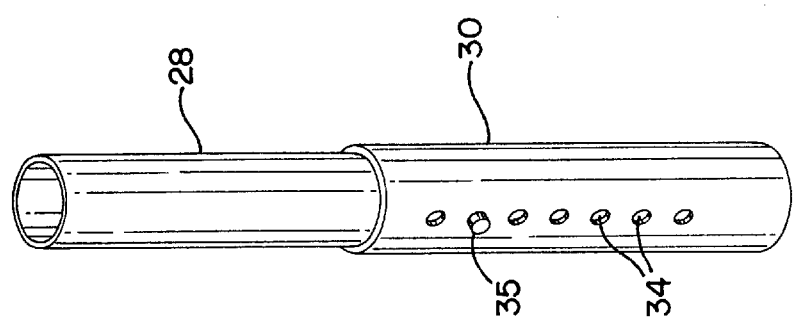
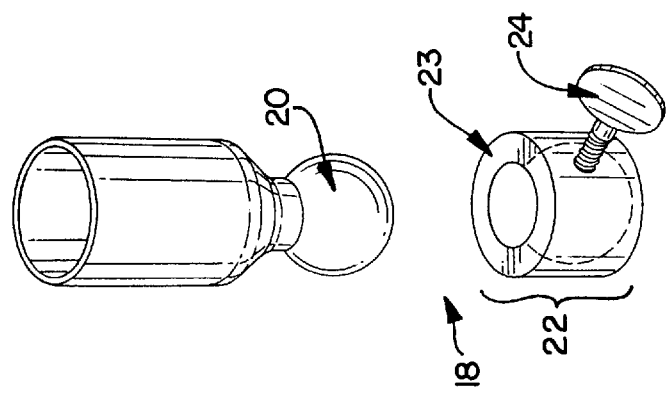

ANTERIOR SUPPORT DEVICE

FIELD OF THE INVENTION

The present invention is directed generally to a support device and specifically to an anterior support device for use in the health care industry.

BACKGROUND OF THE INVENTION

Many individuals suffer from lower back pain and dysfunction brought about by their work environment or other daily activities. Repetitive or prolonged activities can be attributed as a major cause of this back pain and dysfunction. Effected individuals must drastically modify their work areas in order to continue their jobs. In many instances, people must choose another field of employment.

One such example is dentists. Dentists spend a good deal of their workday leaning over patients, in a forward bent position. This position contributes to posterior disc dysfunction, which leads to back pain and disability. For dentists, back pain is one of the leading causes of early retirement.

To alleviate such back pain, some individuals turn to physical therapy. Others attempt to support their backs while on the job by using braces and cushions that are intended to support the spine in a normal, anatomical position. These devices, however, are designed to support the individual from the rear and thus are not effective for dentists and similar professionals who must be in a forward, bent position as a fundamental part of their work.

Thus, there is a need in the art for a device that supports an individual's spine while the individual is in a forward bent position.

There is a further need in the art for a device that decreases the stress on the lower, mid, and upper back experienced by an individual while in a forward bent position.

There is yet a further need in the art for a device that extends the productive life of individuals who perform repetitive or prolonged activities as part of their employment or daily activities.

SUMMARY OF THE INVENTION

The present invention meets the needs of the prior art by providing a device that supports an individual's spine while the individual is in a forward bent position. The device includes a padded rest on which an individual could lean while working in a forward bent position and brackets for adjusting the angle, height, and position of the device. Since the individual leans against the rest, the stresses experienced in the lower, middle and upper back are substantially decreased. Reducing such stress decreases the pain experienced by the individual as well as extends his or her productive life.

BRIEF DESCRIPTION OF THE DRAWINGS

FIG. 1 is a perspective view of the present invention in use with a dentist's chair.

FIG. 2 is a front view of the device shown in FIG. 1.

FIG. 3 is a perspective view of an alternate embodiment of the present invention in use with a desk.

FIG. 4 is a perspective view of an alternate attachment for the embodiment of FIG. 3.

FIG. 5 is a partially exploded, perspective view of another alternate embodiment of the present invention for use in activities such as gardening.

FIG. 6 is a partially exploded, perspective view of the coupler used in the present invention.

FIGS. 7a and 7b are perspective views of the telescoping feature of the present invention.

DETAILED DESCRIPTION OF THE INVENTION

Figure 8:
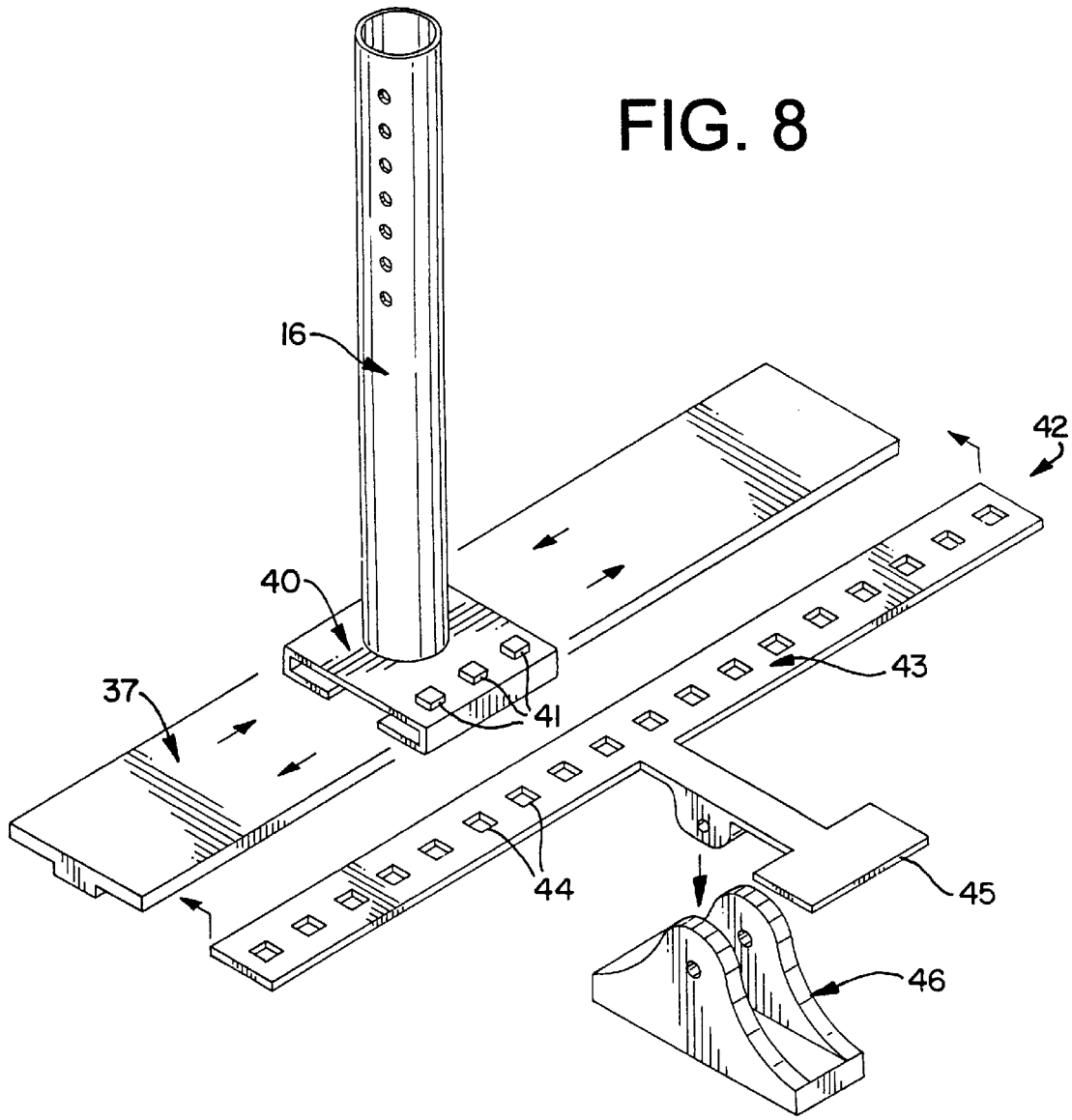
FIG. 8 is a partially exploded, perspective view of the coupling and locking mechanisms of the present invention for use with a dentist's chair.

As depicted in the figures, the device 10 of the present invention generally includes a padded rest 12, an angled bracket 14, and an upright bracket 16. The padded rest 12 may pivot with respect to the angled bracket 14. This pivoting is enabled due to the presence of a single or multi-axial pivot device 19, as depicted in FIG. 2.

As can be best seen from FIG. 2, the bracket 14 extends at an angle from the upright bracket 16 so that the rest 12 is positioned to support the practitioner near the patient. To accomplish this, a coupler 18 is provided between the angled bracket 14 and the upright bracket 16 to allow the rest 12 to be tilted in any direction. Once the angular position of the bracket 14 with respect to the upright bracket 16 is adjusted to the desired position, the coupler 18 locks the angled bracket 14 in that position.

Preferably, the coupler 18 takes the form of a ball swivel 20 with a screw friction lock 22, as shown in detail in FIG. 6. The friction lock 22 comprises a retainer 23 into which the ball end of the bracket is inserted and a screw tightener 24 for locking the bracket in the desired position.

Brackets 14 and 16 may be adjustable in length so that the distance of the rest 12 from the patient can be varied. Although the figures depict both brackets as adjustable in length, the present invention contemplates having only one adjustable bracket. To enable this adjustability, at least one of the brackets 14, 16 comprises a first bracket member 28 carrying a spring-loaded pin lock 35 and a second bracket member 30 including a plurality of adjusting holes 34. The details of this feature can be seen in FIGS. 7a and 7b. The first member 28 mates with, and telescopes with respect to, the second member 30. This telescoping allows the overall height of the respective bracket to be adjusted. Once the desired height of the bracket is obtained, the pin 35 springs into one of the holes 34 of the second bracket member 30, as shown in FIG. 7a. The pin 35 functions to lock bracket member 28 at the desired height with respect to bracket member 30. Thus, the overall height of the device can be varied by adjusting the length of one or both the brackets 14, 16.

Although not shown in FIGS. 7a and 7b, member 28 is provided with two spring loaded pin locks 35, one on each side of the member. Similarly, member 30 is provided with two sets of adjusting holes 34, the sets being 180 degrees apart. Therefore, the member 28 is held at the desired height by the interaction of both pin locks 35 with their respective set of adjusting holes 34. This further ensures that the bracket remains at the desired height.

As can be seen in FIGS. 1 and 2, the lower end of the bracket 16 is operatively coupled to a track 37 positioned adjacent the base of the dental chair 38. Referring to FIG. 8, the lower end of the bracket 16 may be provided with a slide plate 40 for coupling or riding along the track 37, the slide plate 40 including raised locking pins 41. The coupling of the bracket 16 along the track 37 allows the device to be moved along the base of the chair 38.

To lock the bracket 16 in the desired position along the track 37, a foot-controlled lock 42 is provided. Lock 42 comprises a spring-loaded locking bar 43 and a pivot mounting 46. The locking bar 43 includes a series of locking holes 44 and a footplate 45 extending from the bar. When the bracket 16 is in the locked position, the locking bar 43 is positioned above the slide plate 40, with the locking holes 44 engaging the raised locking pins 41 of the slide plate 40. To release the bracket 16 from the locked position, the professional steps down on the footplate 45, thereby causing the locking bar 43 to pivot about the mounting 46. This pivoting further results in the locking pins 41 disengaging the locking holes 44. The bracket 16 can now be moved to a new position along the track 37. To lock the bracket 16 in the new position, the professional merely releases the footplate 45. The footplate 45 is biased into contact with the slide plate 41, the holes 44 again engaging the pins 41. Thus, the position of the device 10 may be changed to accommodate the preference of the professional or the particular patient.

The padded rest 12 can be used by a professional such as a dentist or a dental hygienist to lean over a patient while working on the patient. Since the back of the professional is supported while in this bent position, the stress experienced by the professional in his or her lower, mid, and upper back is reduced. Because the source of the support is anterior, the professional can assume any degree of forward lean to accomplish the required task and still be supported.

Due to bracket 14, the padded rest 12 can be tilted in any direction to accommodate a particular body type or gender. The amount of padding is variable to allow the professional to change the contact points of the rest. Depending upon the comfort and preference of the professional, the rest may contact the professional in the abdominal, chest, or anterior shoulder areas.

To use the present invention, the professional adjusts the angle of the bracket 14, the height of the bracket 14 and/or bracket 16, and the position of the bracket 16 with respect to the dental chair 38. Then the professional can lean forward against the rest 12, while working on the patient. Alternately, the professional can sit in a chair and lean against the rest 12 to work on the patient. Because the professional is allowed to lean against the rest 12, the back stresses experienced by the professional are reduced.

The present invention is not limited to use in the dental setting. Such a device may be beneficial in other fields in which individuals spend much of their day in the forward bent position. For example, a lab technician who spends much of the day leaning over a bench could benefit from the present invention. In addition, the present invention may be helpful to others, such as individuals who lean forward over a countertop, desktop or workbench during the course of the day.

For example, FIG. 3 depicts an alternate embodiment 48 of the present invention in use with a desk, table or workbench 50. The embodiment 48 generally comprises a padded rest 52 and an upright bracket 54. To adjust the angle of the rest 52, a ball swivel (not shown) with a screw friction lock (not shown), as depicted in FIG. 6, is provided between the rest 52 and the bracket 54. The bracket 54 is also provided with the telescoping feature of FIGS. 7a and 7b, thereby making it adjustable in height. To allow the horizontal position of the bracket 54 with respect to the desk 50 to be adjusted, the lower end of the bracket 54 is provided with a slide member 62 and the desk 50 with a track member 64. The slide member 62 rides along the track member 64 in a conventional manner. To lock the bracket 54 in a certain position along the track 64, a friction lock 68 is engaged. Alternately, the lower end of the bracket 54 may be provided with a "C-clamp" type mount 70, as shown in FIG. 4. Such a clamp 70 along with a ball joint pivot would mount the device directly to the edge of the desk or workbench 50.

FIG. 5 depicts yet a further embodiment 80 of the present invention for use in gardening or activities involving kneeling. Such a device may include a padded rest 82, a vertical adjustable bracket 84, and a footplate 86 at the lower end of the bracket 84. The padded rest 82 may also include a neck or shoulder strap 88 for carrying the device, thereby allowing the user to change positions without the use of his hands.

The device may be provided with a coupling 90 between the rest 82 and the bracket 84 to vary the angle of the rest 82 with respect to the bracket 84. In addition, a coupling 92 may also be provided between the bracket 84 and the footplate 86. These couplings may take the form of a ball swivel with a screw friction lock, similar to that shown in FIG. 6. The bracket 84 may also be provided with the telescoping feature, shown in FIGS. 7a and 7b, to allow the height of the bracket 84 to be adjusted.

While the invention has been described in connection with certain embodiments, it should be understood that it is not intended to limit the invention to these particular embodiments. To the contrary, it is intended to cover all alternatives, modifications and equivalents falling within the spirit and scope of the invention.

What is claimed is:

1. A support device for use with a dental chair comprising:
   a rest against which a user can lean to relieve back stress;
   an angled bracket operatively coupled at a first end to the rest; and
   an upright bracket operatively coupled at a first end to the angled bracket and at a second end to a base of the dental chair,
   wherein the brackets enable the angle of the rest, a height of the rest, and a position of the rest with respect to the dental chair to be adjusted.

2. The support of claim 1 wherein the rest includes padding.

3. The support of claim 2 wherein an amount of padding can be adjusted.

4. The support of claim 1 wherein the angled bracket extends at an angle with respect to the upright bracket.

5. The support of claim 4 further comprising a coupler between the angled bracket and the upright bracket that allows the angled bracket to extend at a variable angle with respect to the upright bracket.

6. The support of claim 5 wherein the coupler includes a ball swivel and a screw lock to lock the angled bracket in a desired angled position.

7. The support of claim 1 wherein a length of the angled bracket is adjustable.

8. The support of claim 1 wherein a length of the upright bracket is adjustable.

9. The support of claim 1 further comprising a track provided adjacent the base of the dental chair, the second end of the upright bracket being operatively coupled to the track.

10. The support of claim 9 wherein the second end of the upright bracket is provided with a slide plate for cooperating with the track to vary a position of the support with respect to the dental chair, the slide plate including a plurality of locking pins.

11. The support of claim 10 further comprising a foot-controlled lock for locking the upright bracket in a desired position along the track.

12. The support of claim 11 wherein the foot-controlled lock comprises a spring-loaded locking bar and a pivot mounting.

13. The support of claim 11 wherein the locking bar includes a series of locking holes and a footplate extending from the bar, the locking holes engaging the locking pins of the slide plate when the upright bracket is in the locked position.

14. The support of claim 1 wherein at least one of the brackets further comprises a first bracket member and a second bracket member, the first bracket member mates with, and telescopes with respect to, the second bracket member.

15. The support of claim 14 wherein the second bracket member is provided with a plurality of holes.

16. The support of claim 15 wherein the first bracket member is provided with a spring-biased pin for interacting with one of the holes of the second bracket member to lock the bracket at a desired length.

* * * * *

UNITED STATES PATENT AND TRADEMARK OFFICE
CERTIFICATE OF CORRECTION

PATENT NO. : 6,435,186 B1
DATED : August 20, 2002
INVENTOR(S) : Kurt Klemm

It is certified that error appears in the above-identified patent and that said Letters Patent is hereby corrected as shown below:

<u>Column 4,</u>
Lines 33-34, should read -- an angle of the rest, a height of the rest, and a position of the rest --

Signed and Sealed this

Fifth Day of August, 2003

JAMES E. ROGAN
*Director of the United States Patent and Trademark Office*